United States Patent
Miyamoto et al.

(10) Patent No.: US 8,496,641 B2
(45) Date of Patent: *Jul. 30, 2013

(54) FASTENING MEMBER COMPRISING SHAPED TAB

(75) Inventors: Kouichi Miyamoto, Kobe Hyogo (JP); Joseph Bernard Kraimer, Kobe Hyogo (JP); David Randall Knaub, Portland, OR (US); Jason Arthur Hilbourne, Portland, OR (US); Henry Young Chin, Portland, OR (US)

(73) Assignee: The Procter & Gamble Company, Cincinnati, OH (US)

( * ) Notice: Subject to any disclaimer, the term of this patent is extended or adjusted under 35 U.S.C. 154(b) by 20 days.

This patent is subject to a terminal disclaimer.

(21) Appl. No.: 13/276,526

(22) Filed: Oct. 19, 2011

(65) Prior Publication Data
US 2012/0035579 A1     Feb. 9, 2012

Related U.S. Application Data

(63) Continuation of application No. 12/492,223, filed on Jun. 26, 2009, now Pat. No. 8,060,993, which is a continuation of application No. 11/796,846, filed on Apr. 30, 2007, now Pat. No. 7,568,264, which is a continuation of application No. 10/624,005, filed on Jul. 21, 2003, now Pat. No. 7,219,403.

(60) Provisional application No. 60/398,002, filed on Jul. 23, 2002.

(51) Int. Cl.
*A61F 13/15*     (2006.01)

(52) U.S. Cl.
USPC ...... 604/391; 604/389; 604/390; 604/385.29; 604/385.3; 24/442; 24/306; 24/450; 24/452; 428/100

(58) Field of Classification Search
USPC .... 604/391, 390, 389, 385.29, 385.3; 24/442, 24/306, 450, 452; 428/100
See application file for complete search history.

(56) References Cited

U.S. PATENT DOCUMENTS 4,568,344 A * 2/1986 Suzuki et al. ............ 604/389
4,670,960 A   6/1987 Provost
(Continued)

FOREIGN PATENT DOCUMENTS

DE    196 52 742 A1 *   6/1998
EP       755665 A1 *    1/1997
(Continued)

OTHER PUBLICATIONS

U.S. Appl. No. 10/624,005, filed Jul. 21, 2003, All Office Actions and Responses through May 22, 2007.
(Continued)

*Primary Examiner* — Tatyana Zalukaeva
*Assistant Examiner* — Ginger T Chapman
(74) *Attorney, Agent, or Firm* — Thibault Fayette

(57) ABSTRACT

A fastening member used for, e.g., a disposable absorbent article is disclosed. The fastening member extends in a longitudinal direction and in a lateral direction and has a lateral centerline. The fastening member comprises a base panel and a shaped tab extending laterally from the base panel. The shaped tab has a longitudinal centerline, a lateral centerline, a distal portion and a proximal portion. The shaped tab has a contour edge comprising a shaped upper edge and a shaped lower edge. The shaped upper edge and the shaped lower edge are symmetric with respect to the longitudinal centerline of the shaped tab when relatively shifted in the longitudinal direction and are asymmetric with respect to the lateral centerline of the fastening member.

20 Claims, 12 Drawing Sheets

U.S. PATENT DOCUMENTS

| | | | |
|---|---|---|---|
| 5,019,073 A | 5/1991 | Roessler et al. |
| 5,151,092 A | 9/1992 | Buell et al. |
| 5,312,387 A | 5/1994 | Rossini et al. |
| 5,383,871 A | 1/1995 | Carlin et al. |
| 5,399,219 A | 3/1995 | Roessler et al. |
| 5,477,249 A | 12/1995 | Hotomi |
| 5,580,411 A | 12/1996 | Nease et al. |
| 5,603,708 A | 2/1997 | Seth |
| 5,603,794 A | 2/1997 | Thomas |
| 5,725,714 A | 3/1998 | Fujioka et al. |
| 5,759,317 A | 6/1998 | Justmann |
| 5,828,393 A | 10/1998 | Hotomi |
| 5,876,531 A | 3/1999 | Jacobs et al. |
| 5,897,545 A | 4/1999 | Kline et al. |
| 5,985,081 A | 11/1999 | Reynolds |
| 6,051,094 A | 4/2000 | Melbye et al. |
| 6,230,374 B1 | 5/2001 | Widlund |
| 6,454,751 B1 | 9/2002 | Olson |
| 7,219,403 B2 | 5/2007 | Miyamoto et al. |
| 7,371,302 B2 | 5/2008 | Miyamoto et al. |
| 7,568,264 B2 | 8/2009 | Miyamoto et al. |
| 2003/0009144 A1 | 1/2003 | Tanzer et al. |
| 2004/0022998 A1 | 2/2004 | Miyamoto et al. |
| 2007/0234530 A1 | 10/2007 | Miyamoto et al. |

FOREIGN PATENT DOCUMENTS

| | | | |
|---|---|---|---|
| FR | 2810537 A1 | * | 12/2001 |
| GB | 2284742 A | * | 6/1995 |
| GB | 2296179 A | * | 6/1996 |
| JP | 2003/135110 A | | 5/2003 |
| WO | WO 2005016199 A1 | * | 8/2005 |
| WO | WO 2005016211 A1 | * | 8/2005 |

OTHER PUBLICATIONS

U.S. Appl. No. 11/796,846, filed Apr. 30, 2007, All Office Actions and Responses through Jul. 15, 2009.

* cited by examiner

FASTENING MEMBER COMPRISING SHAPED TAB

CROSS REFERENCE TO RELATED APPLICATIONS

This application is a continuation of prior U.S. application Ser. No. 12/492,223, filed Jun. 26, 2009, now U.S. Pat. No. 8,060,993 which is a continuation of U.S. application Ser. No. 11/796,846, Apr. 30, 2007, now U.S. Pat. No. 7,568,264, issued Aug. 4, 2009, which is a continuation of prior U.S. application Ser. No. 10/624,005, filed Jul. 21, 2003, now U.S. Pat. No. 7,219,403, issued May 22, 2007, which claims tee benefit of U.S. Provisional Application No. 60/398,002, filed Jul. 23, 2002, the substances of which are incorporated herein by reference.

TECHNICAL FIELD

The present invention relates to a fastening member comprising a base panel and a shaped tab extending from die base panel. More specifically the present invention relates to a fastening member which may be used for fastening a portion of an object to another portion.

BACKGROUND

Fastening systems am widely known and widely used. Disposable absorbent articles are one example which is provided with fastening systems. The fastening systems provided on disposable absorbent articles are to form a closure of so-called open type absorbent articles (e.g., diaper) when in use or to adjust the dimension of the waist circumference of so-called pull-on type absorbent articles (e.g., diaper). In conventional arrangement of fastening systems on disposable diapers, the fastening member of the fastening system is provided to extend in the direction parallel to the lateral direction of the absorbent diaper such that the fastening member is polled in the lateral direction for fastening the diaper and for forming a defined dimension of die waist opening. This provides a lateral tensioning force to keep the diaper in the abdominal region of the wearer. However, this defined waist dimension created by the fastening system cannot accommodate the changes in body dimension caused by wearer movement such that the diaper tends to slide/slip down on the wearer when the dimension of the abdomen of the wearer becomes smaller than the defined dimension formed by the fastening system. Further, when the abdominal dimension becomes larger than the defined dimension formed by the fastening system, the body tends to push the diaper to a different position on the wearer (typically to a smaller dimension area which is lower than the point of initial fit) or the diaper tends to be so tight on the abdomen that the diaper can mark the skin or be uncomfortable to wear.

Many attempts have been made to solve such problems. U.S. Pat. No. 5,383,871 issued to Carlin et al. on Jan. 24, 1995 discloses a closure system for anchoring the absorbent, article on the wearer. The closure system provides a primary line of tension around the wearer that fits predominantly within the low motion zone to enhance the dynamic fit and to anchor the absorbent core in place so that it will not slip/slide during use. The primary hoc of tension established by the closure system is disposed at an angle on the wearer. In preferred embodiments, the closure system is provided with tape tabs of a specified design, to allow the wearer to easily form the "angled" primary line of tension about the wearer. U.S. Pat. No. 5,603,794 issued to Thomas on Feb. 18, 1997 discloses a method for the manufacture of angled tape tabs for use with disposable absorbent articles. The tape tabs are provided at an angle to the machine direction or longitudinal centerline of the disposable diaper to provide improved fit and containment about the wearer's waist. However, these publications do not disclose a specific design of tape tab to allow easy and inexpensive operation of manufacture without creating a trim while providing directionality of the tape tab.

Based on the foregoing, there is a need for a fastening member which is able to provide directionality of the fastening member. There is also a need for a fastening member which is able to be easily and inexpensively manufactured without creating a trim. None of the existing absorbent articles provides all of the advantages and benefits of the present invention.

SUMMARY

The present invention is directed to a fastening member. The fastening member extends in a longitudinal direction and in a lateral direction and has a lateral centerline. The fastening member comprises a base panel and a shaped tab extending laterally from the base panel. The shaped tab has a longitudinal centerline, a lateral centerline, a distal portion and a proximal portion. The shaped tab has a contour edge comprising a shaped upper edge and a shaped lower edge. The shaped upper edge and the shaped lower edge are symmetric with respect to the longitudinal centerline of the shaped tab when relatively shifted in the longitudinal direction and are asymmetric with respect to the lateral centerline of the fastening member.

All documents cued are, in relevant part, incorporated herein by reference; the citation of any document is not to be construed as an admission that it is prior an with respect to the present invention.

BRIEF DESCRIPTION OF THE DRAWINGS

While the specification concludes with claims particularly pointing out and distinctly claiming the invention, it is believed that the present invention will be better understood from, the following description of preferred embodiments takes in conjunction with the accompanying drawings in which;

DETAILED DESCRIPTION

As used herein, the term "comprising" means that other steps and other ingredients which do not affect die end result can be added. This term encompasses the terms "consisting of" and "consisting essentially of."

As used herein, the term "absorbent article" refers to devices which absorb and contain body exudates, and more specifically, refers to devices which are placed against or in proximity to the body of the wearer to absorb and contain the various exudates discharged from the body. The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner). As used herein, the term "disposed" is used to mean mat an element(s) of the diaper is formed (joined and positioned) in a particular place or position as a unitary structure with other elements of the diaper or as a separate element joined to another element of the diaper. As used herein, the term "joined" encompasses configurations whereby an element is directly secured to another element by affixing the element directly to the other element, and configurations whereby an element is indirectly secured to another element by affixing the element to intermediate members) which in turn are affixed to the other element.) As used herein, the terra "diaper" refers to an absorbent article generally wont by infants and incontinent persons about, the lower torso. The present invention is also applicable to other absorbent articles such as incontinence briefs, incontinence undergarments, absorbent inserts, diaper holders and liners, feminine hygiene garments, and the like. The term "longitudinal", as used herein, refers to a line, axis or direction in the plane of the absorbent article that is generally aligned with (e.g., approximately parallel to) a vertical plane which bisects a standing wearer into left and right body halves when the absorbent article Is worn. The terms "transverse" or "lateral" used herein, are interchangeable, arm refer to a line, axis or direction which lies within the plane of the absorbent article that is generally perpendicular to the longitudinal direction.

Figure 1:
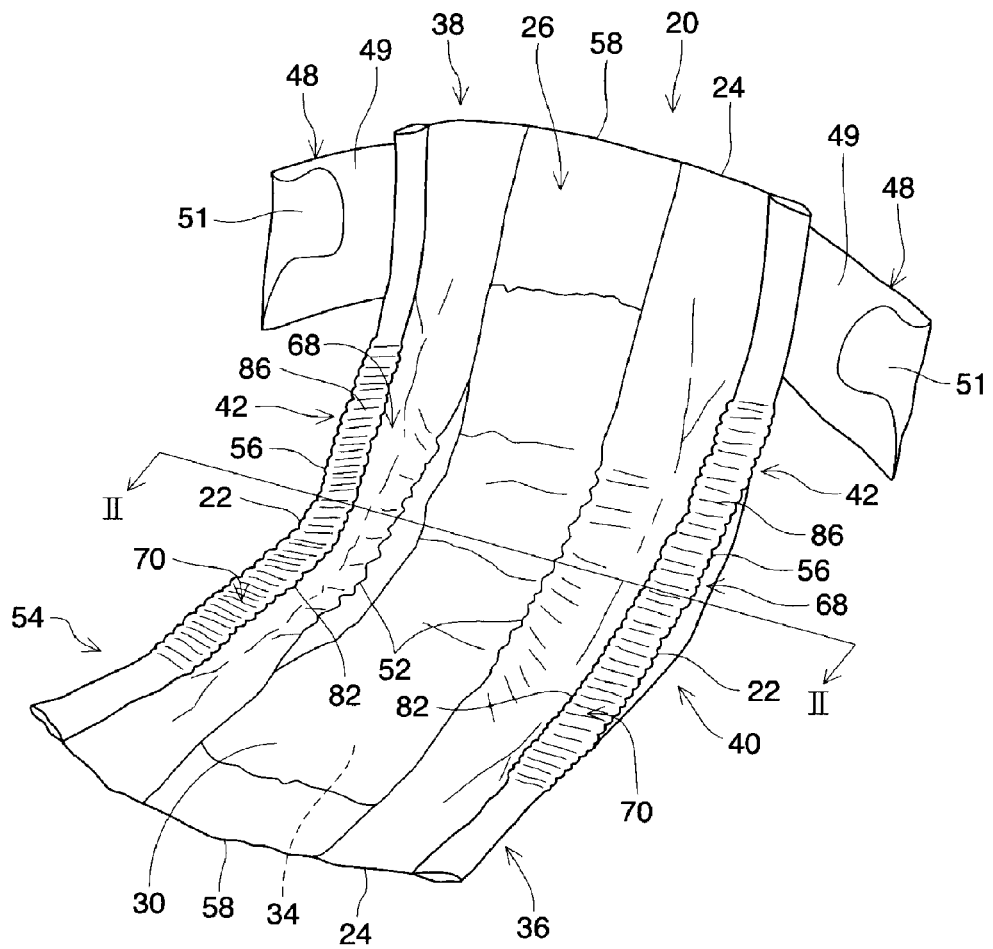
FIG. 1 is a perspective view of one embodiment of a diaper having a fastening member of the present invention.
Figure 2:
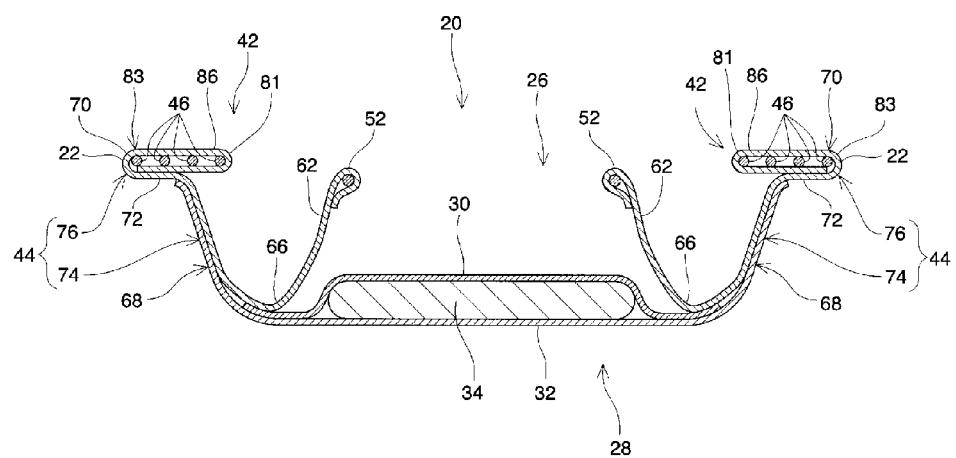
FIG. 2 is a cross-sectional view taken along the line II-II of FIG. 1.
Figure 3:
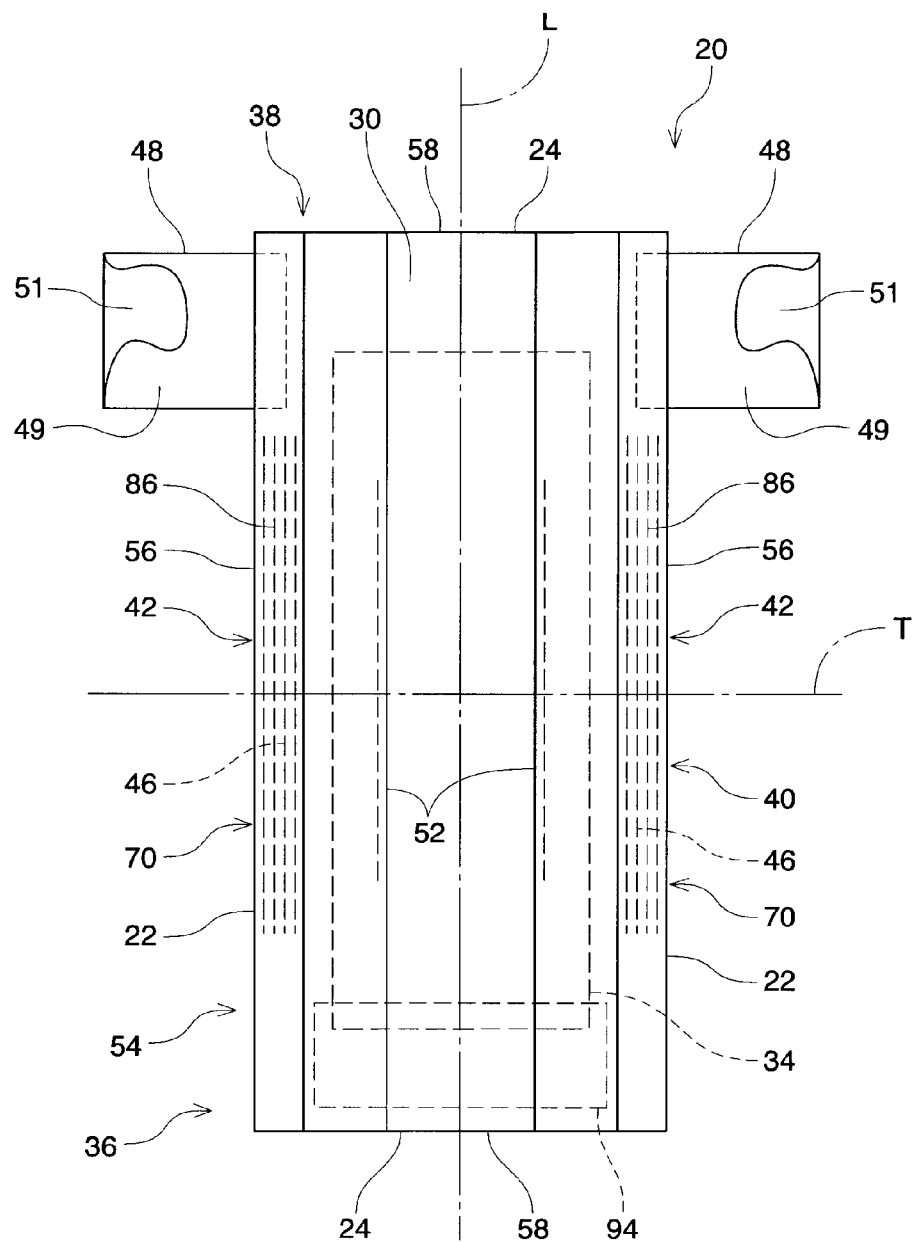
FIG. 3 is a top plan view of the diaper of FIG. 1 in its flat-out configuration.

FIG. 1 is a perspective view of the diaper 20 having a fastening member 48 of the present invention. Referring to FIG. 2 showing a cross-sectional view taken along the line II-II of FIG. 1 and FIG. 3 showing a top plan view of the diaper 20 of FIG. 1 in its flat-out configuration as well, the diaper 20 has an Inner surface 26 facing the wearer, an opposite outer surface 28, a longitudinal centerline L, and a lateral centerline T. The diaper 20 also has longitudinal side edges 22 run generally in the longitudinal direction of the diaper and lateral end edges 24 run between the longitudinal side edges 22 generally in the lateral direction of the diaper 20. The periphery of the diaper 20 is defined by the longitudinal side edges 22 and the lateral end edges 24. The diaper 20 further has a from waist region 36, a back waist region 38 and a crotch, region 40 disposed between the front waist region 36 and the back waist region 38.

The diaper 20 comprises a chassis 54 and a fastening member 48 joined to the chassis 54. The chassis 54 has a generally rectangle shape in its flat-out configuration as shown in FIG. 3. The chassis 54 has lateral end edges 58 and longitudinal side edges 56. The lateral end edge 58 of the chassis 54 preferably defines the lateral end edge 24 of the diaper 20. The longitudinal side edges 56 of the chassis 54 preferably defines the longitudinal side edge 22 of the diaper 20 at least in the crotch region 40. The chassis 54 comprises a liquid pervious topsheet 30; a liquid impervious backsheet 32; an absorbent core 34, which is preferably positioned between at least a portion of the topsheet 30 and the backsheet 32; and a side flap 44 extending laterally outwardly from the absorbent core 34, The side flap 44 has a proximal flap 74 and a distal flap 76. The chassis 54 further comprises an elasticized outer leg cuff 42 disposed adjacent to the longitudinal side edge 22 in the crotch region 40, The elasticized outer leg cuff 42 has a base 68 and a gasket cuff 70 supported by the base 68 at a joint 72 of the base 68 to the gasket cuff 70. The gasket cuff 70 is provided with an elastic material 46 and has an inner cuff 81 extending laterally inwardly from the joint 72 and an outer cuff 83 extending laterally outwardly from die joint 72. The chassis 54 shown in FIG. 1 also may comprise barrier leg cuffs 52 and an elastic waist feature (not shown in Figures). The fastening member 48 is joined adjacent to the longitudinal side edge 56 of die chassis 54 and joined to an element constituting the chassis 54 such as a topsheet, a backsheet, an absorbent core, an elastic-feed outer leg cuff, a barrier leg cuff or combinations thereof by any known means such as adhesives or heat and pressure attachment such that the fastening member 48 extends laterally outwardly from the absorbent core 34. In the embodiment shown in FIG. 1, the fastening member 48 is joined to the backsheet 32 by heat and pressure attachment. The fastening member 48 comprises an ear panel or base panel 49 and a shaped tab 51 extending laterally outwardly from the ear panel 49 in stretched configuration of the shaped tab 51 (FIGS. 1 and 3 show the shaped tab 51 being folded laterally inwardly). The fastening member 48 also has fastening materials 100. A landing zone member 94 is provided in the front waist region 36 to form a closure of the diaper 20 together with the fastening materials 100 of the fastening member 48.

The liquid pervious topsheet 30 is preferably positioned adjacent the body-facing surface of the absorbent core 34 and may be joined thereto anchor to the backsheet 32 by any attachment means known in the art. The topsheet 30 is preferably compliant, soft feeling, and non-irritating to the wearer's skin. Further, at least a portion of the topsheet 30 is liquid pervious, permitting liquid to readily penetrate through its thickness. A suitable topsheet 30 may be manufactured from, a wide range of materials, such as porous foams; reticulated foams; apertured plastic films; or woven or nonwoven webs of natural fibers (e.g., wood or cotton fibers), synthetic fibers (e.g., polyester or polypropylene fibers), or a combination of natural and synthetic fibers. Preferably, the topsheet 30 is made of a hydrophobic material or is treated to be hydrophobic in order to isolate the wearers skin from liquids contained in the absorbent core 34. If the topsheet 30 is made of a hydrophobic material, preferably at least the upper surface of the topsheet 30 is treated to be hydrophilic so that liquids will transfer through the topsheet more rapidly.

The liquid impervious back sheet 32 is generally that portion of the diaper 20 positioned adjacent the gamiest-facing surface of the absorbent core 34. Backstreet 32 prevents the exudates absorbed and contained therein from soiling articles that may contact the diaper 20, such as bedsheets and undergarments. In preferred embodiments, the backsheet 32 is impervious to liquids (e.g., urine) and comprises a thin plastic film such as a thermoplastic film having a thickness of about 0.012 mm (0.5 mil) to about 0.051 mm (3.0 mils). Suitable backsheet films include those manufactured by Tredegar Industries Inc. of Terre Haute, Ind. and sold under the trade names X15306, X10962, and X10964. Other suitable backsheet materials may include breathable materials that permit vapors to escape from the diaper 20 while still preventing exudates from passing through the backsheet 32. Exemplary breathable materials may include materials such as woven webs, nonwoven webs, composite materials such as film-coated nonwoven webs, and microporous films such as manufactured by Mitsui Toatsu Co., of Japan under the designation ESPOIR NO and by EXXON Chemical Co., of Bay City, Tex., under the designation EXXAIRE. Suitable breathable composite materials comprising polymer blends am available from Clopay Corporation, Cincinnati, Ohio under the name HYTREL blend P18-3097. The backsheet 32 may be covered by a woven or a nonwoven to impart more cloth-like appearance to the diaper.

The absorbent core 34 may comprise any absorbent material that is generally compressible, conformable, non-irritating to the wearer's skin, and capable of absorbing and retaining liquids such as urine and other certain body exudates. The absorbent core 34 has longitudinal side edges and end edges and can be manufactured in a wide variety of sizes and shapes (e.g., rectangular, hourglass, "T"-shaped, asymmetric, etc.) and may comprise a wide variety of liquid-absorbent materials commonly used in disposable diapers and other absorbent articles such as comminuted wood pulp, which is generally referred to as airfelt. Examples of other suitable absorbent materials include creped cellulose wadding; meltblown polymers, including coform; chemically stiffened, modified or cross-linked cellulosic fibers; tissue, including tissue wraps and tissue laminates; absorbent foams; absorbent sponges; superabsorbent polymers; absorbent gelling materials; or any other known absorbent material or combinations of materials. In any case all or a portion of the core may include slits which allow the core to form openings when stretched into which fecal mater can flow. The configuration and construction of the absorbent core 34 may also be varied (e.g., the absorbent core(s) or other absorbent structure(s) may have varying caliper zones, a hydrophilic gradient, a superabsorbent gradient, or lower average density and lower average basis weight acquisition zones; or may comprise one or more layers or structures). However, the total absorbent capacity of the absorbent core 34 should be compatible with the design loading and the intended use of the diaper 20.

The barrier leg cuff 52 is joined adjacent the longitudinal side edges 56 of the chassis 54, In the embodiment shown in FIG. 2, the barrier leg cuff 52 is joined onto the topsheet 30 at the proximal edge 66 of the barrier leg cuff 52 by any known means. The harrier leg cuff 52 nary comprise any known materials such as a nonwoven material which may be liquid impervious and/or hydrophobic. The barrier leg cuff 52 has a lateral inner portion 62 extending laterally inwardly from the proximal edge 66 and being provided with an elastic materials at the distal, end of the lateral inner portion 62 to space the lateral inner portion 62 upwardly away from the topsheet 30 to serve as a barrier to leakage of body exudates.

The side flap 44 shown in FIGS. 1, 2 and 3 is disposed adjacent the longitudinal side edge 56 of the chassis 54 so as to extend laterally outwardly from the absorbent core 34 in the embodiment shown in FIG. 2. The side flap 44 is preferably formed with a material which is liquid impervious and/or hydrophobic. The side flap 44 has a proximal flap 74 which is laterally proximate to the absorbent core 34 and a distal flap 76 which extends laterally outwardly from the proximal flap 74. The proximal flap 74 and the distal flap 76 may be formed with an integral material or alternatively may be formed with separate materials joined to each other. The side flap 44 may be formed by a single layer of material, or two or more layers of material.

The elasticized cater leg cuff 42 shown in FIGS. 1, 2 and 3 comprises the side flap 44 and the elastic material 46. The outer leg cuff 42 is a generally T-shaped cuff having a base 68 and a gasket cuff 70 supported by the base 68 at a joint 72 of the base to the gasket cuff 70. The term "generally T-shaped" means that the base branches from the gasket cuff at the joint between the inner cuff and the outer cuff of the gasket cuff such that the base forms an angle with the inner cuff and an angle with an outer cuff in a cross-sectional view when the diaper is in a relaxed configuration. Therefore, the base may form art angle of 90 degree or an angle other than 90 degree with the inner cuff and the outer cuff. The base 68 comprises the proximal flap 74 and extends between the longitudinal, side edge of the absorbent core 34 and file joint 72. The gasket cuff 70 comprises the distal flap 76 and disposed on tire ton of the base 68, The gasket cuff 70 has an inner cuff 81 extending laterally inwardly from the joint 72 and an outer cuff 83 extending laterally outwardly from the joint 72 as shown in FIG. 2. The top gasket cuff surface 86 has a generally flat surface in cross-section as shown in FIG. 2 while it may have a degree of undulation in the longitudinal direction formed by the gather caused by the elastic material 46 as shown in FIG. 1. The gasket cuff 70 is provided with the elastic material 46 such as a plurality of elastic strands, a single elastic belt or the like.

The fastening member 48 comprises an ear panel or base panel 49 and a shaped tab 51 extending laterally outwardly from the ear panel 49 in stretched configuration of the shaped tab 51. The ear panel 49 and the shaped tab 51 may be formed with an integral material or may be formed with separate materials joined to one another. In the embodiment shown in FIGS. 4 and 5, a portion of the shaped tab 51 is integrally formed with the ear panel 49. The fastening member 48 also has fastening materials 100 to form a closure of the diaper 20 with the landing zone member 94.

The ear panel 49 may comprise any material, such as a plastic film, woven or nonwoven webs of natural fibers (e.g., wood or cotton fibers), synthetic fibers (e.g., polyester or polypropylene fibers), or a combination of natural and synthetic fibers or may comprise any combination of materials thereof. The ear panel 49 is preferably compliant, soft feeling, and non-irritating to the wearer's skin as the ear panel 49 touches the wearer's skin when in use. Further, at least a portion of the ear panel 49 may be vapor pervious, permitting vapor to readily penetrate through its thickness. In the embodiment shown in FIG. 5, the ear panel 49 comprises a plastic film 53 and a nonwoven 55 laminated on the plastic film 53 such that the nonwoven 55 faces the wearer's body and the plastic film 53 faces outwardly when the diaper 20 is used. The ear panel 49 may have stretch ability so that the car panel 49 is able to provide a force to maintain the diaper on the wearers body.

The shaped tab 51 may comprise an extension of the ear panel 49 or may comprise separate materials joined to the ear panel 49. The shaped tab 51 shown in FIG. 5 comprises a leading portion 57, a connective portion 59, and a trailing portion 61. The trailing portion 61 comprises an extension of the ear panel 49. The leading portion 57 may comprise the same material as the ear panel 49 and/or the connective portion 59 or may comprise different materials. The leading portion 57 serves as a grasp portion for the shaped tab 51. The connective portion 59 preferably comprises a material different from the material, of the ear panel 49. This allows to provide the connective portion 59 with properties different from the material of the ear panel 49 with respect to, e.g., stiffness and stretchability. The connective portion 59 may comprise a plastic film, a woven, a nonwoven or a combination thereof. Preferably, the connective portion 59 is stiffer than the ear panel 49. Preferably, the connective portion 59 is less stretch able than the ear panel 49. The connective portion 59 which Is stiffer and/or less stretchable than the ear panel 49 reduces to transmit the forces developed in the ear panel 49 therethrough. It also reduces to transmit the wrinkles created, in the ear panel 49 due to the forces developed in the ear panel 49. The connective portion 49 is provided with an adhesive means 63 to join portions of the connective portion 49 to the trailing portion 61 and the leading portion 57.

The fastening material 100 is provided on the shaped tab 51. The fastening material 100 is intended to provide a fastening means for engaging the landing zone member 94 so as to provide a secure side closure for the diaper 20, Thus, the fastening material 100 comprises a first hook fastening material 106 comprising a plurality of hooks 102 and the base substrate 104 to support the books 102. The base substrate 104 is joined to the connective portion 59 of the shaped tab 51 through the adhesive means 63. It is preferable that the hooks 102 protrude beyond the surface of the ear panel 49 such that the hooks 102 sufficiently engage into the landing zone member 94. It should be understood that the use of the term "book" should be non-limiting in the sense that the engaging elements may comprise any shapes as are known in the art so long as they are adapted to engage a complementary landing zone member. The first hook fastening material 106 may comprise any of the well known configurations and securement means for achieving a side closure on a diaper. It is preferable that the first hook fastening material 106 comprises two book fastening materials which are spaced by positioned in die lateral direction of the shaped tab 51. Each of the first hook fastening materials 106 generally extends in the longitudinal direction of the shaped tab 51 and a gap is provided between each of the first book fastening materials 106. Without wishing to be bound by the theory, it is believed that the gap between the fastening materials contributes to reduce the transmission of the induced stress developed in one of the fastening materials to the other of fastening materials and prevents the other of the fastening materials front being detached due to the transmission of the induced stress developed in the one of The fastening materials. The gap may have a lateral width of between about 3 mm and about 15 mm, preferably between about 5 mm and about 13 mm, more preferably between about 7 mm and about 11 mm. While the fastening material 100 comprises a first hook fastening material 106 comprising a plurality of hooks 102, the fastening material 100 may comprise first adhesive materials which are spacedly positioned in the lateral direction of the diaper 20.

The fastening material 100 may also have a second adhesive material 108 provided at the gap between the first hook fastening material 106. The second adhesive material 108 may comprise the adhesive means 63 of the connective portion 59 or may comprise a different adhesive means. The second adhesive material 108 provides a supplemental fastening means. The second adhesive material 108 may also serve as a means to temporarily attach the shaped tab 51 to the ear panel 49 as shown in FIG. 1 before use of the diaper 20. Alternatively, the second adhesive material 108 may serve as a means to roll up and secure me soiled diaper to dispose it by being joined to the backsheet 32. Such an adhesive material 108 is particularly useful when rite outer surface of backsheet 32 comprises a plastic film as the hook means does not engage the plastic film.

Figure 4:
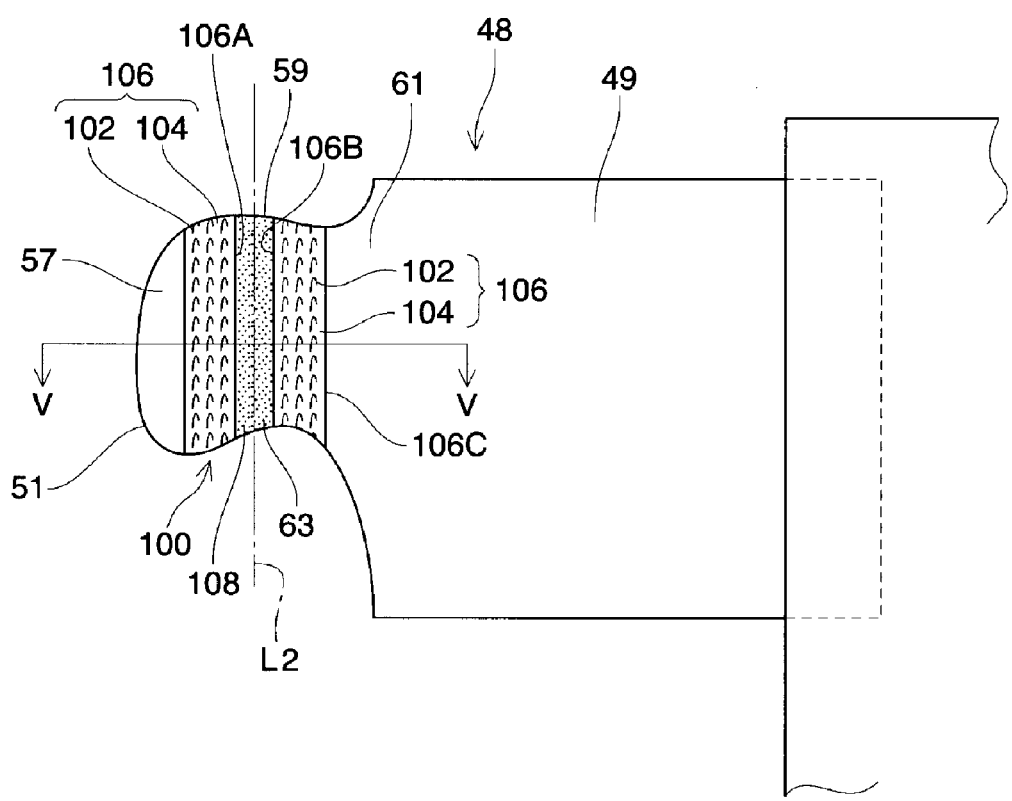
FIG. 4 is an enlarged top plan view of the fastening member.
Figure 5:
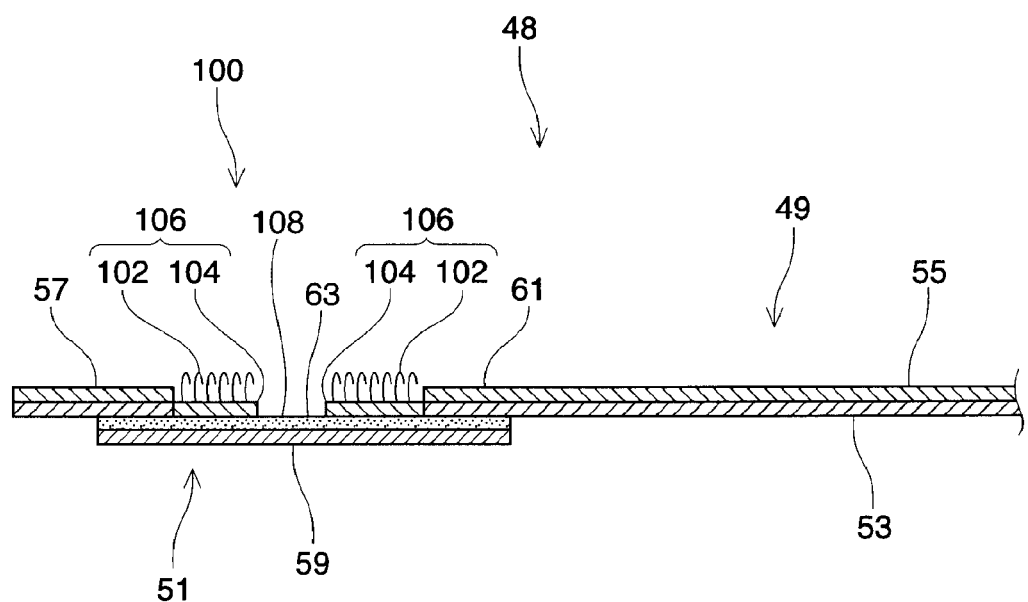
FIG. 5 is a cross-sectional view taken along the line V-V of FIG. 4.

The fastening member 48 may be folded such that the shaped tab 51 having the fastening material 100 is superposed on the ear panel 49 and engages the nonwoven 55 of the ear panel 49 as shown in FIG. 1. In this configuration, the shaped tab 51 may be fielded along the partition line 110 described hereinbelow. Alternatively, the fastening member 48 may be folded at any point of the shaped tab 51 or the ear panel 49. For example, the fastening member 48 may be folded along the line 106 A, 106B or 106C as indicated in FIG. 4. When the fastening member 48 is folded along the line 106A or 106B, the second adhesive material 108 is superposed on either of the first hook fastening materials 106. This allows to prevent the adhesion of the second adhesive material 108 from being deteriorated because the adhesive material 108 only touches the head of the hooks 102.

Figure 6:
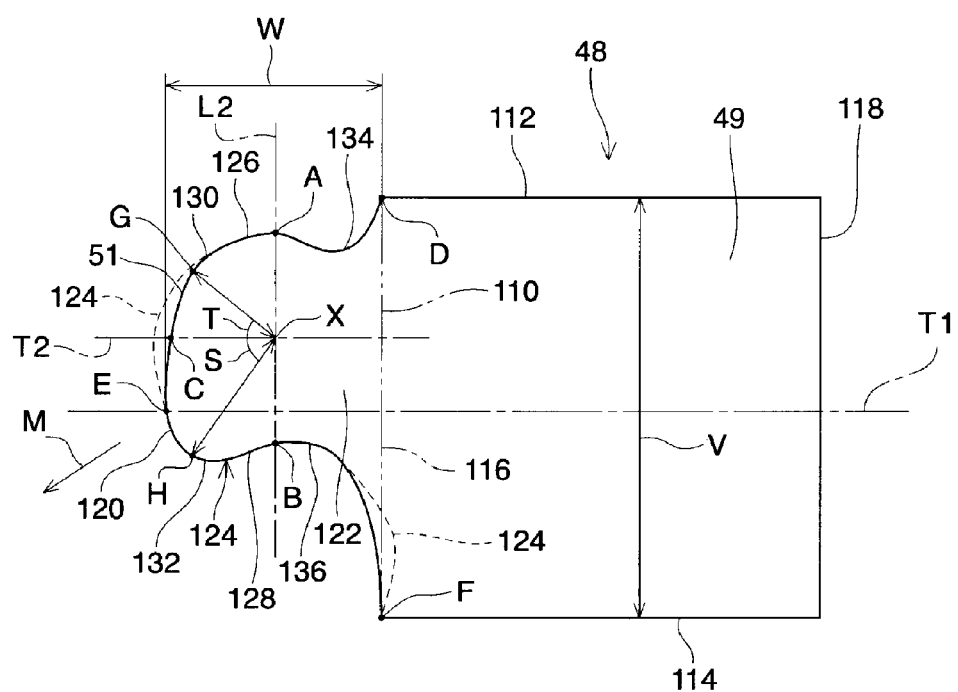
FIG. 6 is a schematic top plan view of the fastening member shown in FIG. 4.

The fastening member 48 is designed to have a specific shape to provide directionality of the fastening member 48 and also to be easily and inexpensively manufactured without creating a trim. FIG. 6 shows an enlarged top plan view of the fastening member 48 comprising the base panel or ear panel 49 and the shaped tab 51. The fastening member 48 extends in the longitudinal direction and in the lateral direction which correspond to the longitudinal direction and the lateral direction of the diaper 20, respectively. The shaped tab 51 is disposed to laterally extend from the base panel or ear panel 49. The ear panel 49 and the shaped tab 51 can be sectioned by a partition line 110 extending In the longitudinal direction as shown in FIG. 6 as an imaginary line. The fastening member 48 also has a lateral centerline T1. The lateral centerline 11 of the fastening member 48 cart be defined as a line extending in the lateral direction equally dividing the partition line 110 into an upper half and a lower half in FIG. 6.

The ear panel 49 has a generally rectangle shape having a lateral upper edge 112, a lateral lower edge 114, a longitudinal leading edge 116 and a longitudinal, trailing edge 118. In the embodiment shown in FIG. 6, the lateral upper edge 112 and a lateral lower edge 114 are in parallel and the longitudinal leading edge 116 and the longitudinal trailing edge 118 are also in parallel. As the lateral upper edge 112 and the lateral lower edge 114 are in parallel, the longitudinal length V of the ear panel 49 should be constant at any point along the lateral direction of the ear panel 49. Such constant longitudinal length V of the ear panel 49 allows not to create any trim when the fastening member 48 is manufactured continuously as described herein below. As far as such constant longitudinal length V of the ear panel 49 is maintained along the lateral, direction, the lateral, upper edge and the lateral lower edge may be curved, wavy, or any other shape. In the embodiment shown in FIG. 6, the partition line 110 aligns the longitudinal leading edge 116. The partition line 110 is defined as a longitudinal line which has the same longitudinal length V as the rest of the ear panel 49 and which is the closest to the shaped tab 51. The longitudinal length in the area of the shaped tab 51 changes depending on the desired shape of the tab and such change of the longitudinal length imparts the "shape" to the shaped tab. In other words, the partition line 110 is the boundary line to start changing the longitudinal length of the fastening member 48 as it moves from the car panel 49 toward the shaped tab 51.

The shaped tab 51 extends laterally from the ear panel 49. The shaped tab 51 is surrounded by a contour edge 124 and the partition line 110. The shaped tab 51 has a longitudinal centerline L2 and a lateral centerline T2. The longitudinal centerline 12 can be defined as a line extending in the longitudinal direction equally dividing the maximum lateral width W of the shaped tab 110 into two. The maximum width W can be determined as a width from the partition line 110 to a point on the contour edge 124 which is laterally furthest, away from partition line 110. The shaped tab 51 also has a distal portion 120 and a proximal portion 122 which are disposed in the lateral direction. The distal portion 120 and the proximal portion 122 may be separated by the longitudinal centerline L2. The lateral centerline 12 can be defined as a line extending in the lateral direction equally dividing the longitudinal centerline L2 into an upper half and a lower half. The longitudinal centerline L2 and the lateral centerline T2 intersect at a center point X. While the partition line 110 shown in FIG. 6 is not disturbed by the contour edge 124 of the shaped tab 51, the partition line 110 may be disturbed by the contour edge 124 as shown by a dotted line in FIG. 6 depending on its shape of the contour edge 124.

The contour edge 124 of the shaped tab 51 comprises a shaped upper edge 126 and a shaped lower edge 128 which are defined by being separated by the lateral centerline T1 of the fastening member 48. Thus, the shaped upper edge 126 extends from a point D where the contour edge 124 and the partition line 110 intersect in the upper half of the fastening member 48 to a point E where the contour edge 124 and the lateral centerline T1 of the fastening member 48 intersect. The shaped lower edge 128 extends from the point E to a point F where the contour edge 124 and the partition line 110 intersects in the lower half of the fastening member 48. The longitudinal centerline L2 intersects the shaped upper edge 126 at a point A in the upper half of the fastening member 48 and intersects the shaped lower edge 128 at anoint B in the rower half of the fastening member 48. The lateral center line 12 intersects the contour edge 124 at a point C.

Figure 7:
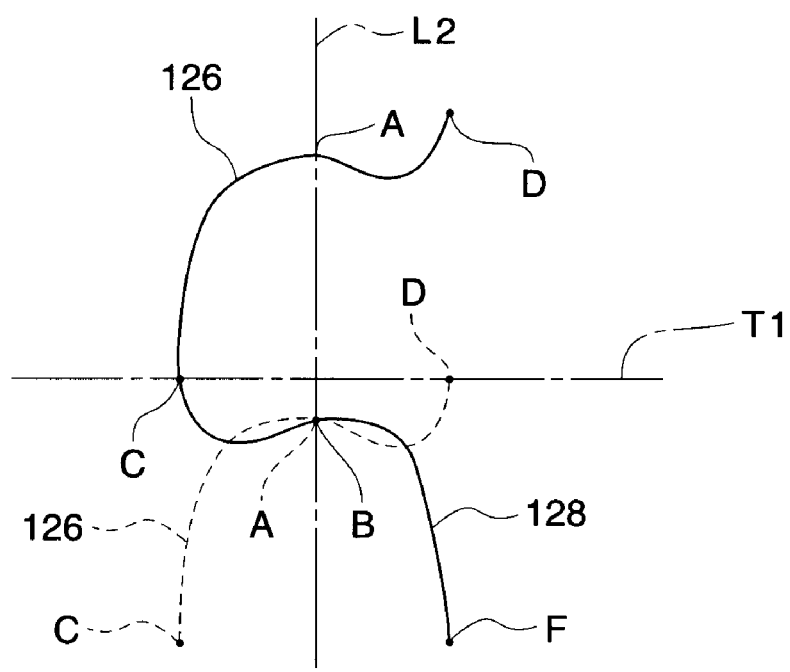
FIG. 7 is a schematic top plan view showing the contour edge of the fastening member.

The shaped upper edge 126 extending between the point D and the point E and the shaped lower edge 128 extending the point E and the point F have specific shapes. It is important that the shaped upper edge 126 and the shaped lower edge 128 are asymmetric with respect to the lateral, centerline T1 of the fastening member 48 as shown in FIG. 7. It is also important that the shaped upper edge 126 and the shaped lower edge 128 are symmetric with respect to the longitudinal centerline L2 of the shaped tab 51 when relatively shifted in the longitudinal direction. As schematically shown in FIG. 7, the shaped upper edge 126 shown by the solid line is relatively shifted in the longitudinal direction toward the shaped tower edge 128 as shown by a dotted imaginary line 126. The dotted imaginary line of the shaped upper edge 126 thus shifted is symmetric with the shaped lower edge 128 with respect to the longitudinal centerline L2 of the shaped tab 51. While the shaped upper edge 126 is relatively shifted in the longitudinal direction in FIG. 7, the shaped lower edge 128 may be relatively shifted In the longitudinal direction toward the shaped upper edge 126.

The specific shapes of the shaped upper edge 126 and the shaped lower edge 128 are important to provide a fastening member which has directionality and which is able to be easily and inexpensively manufactured without creating a trim. The asymmetricalness of the shaped upper edge 126 and the shaped lower edge 128 with respect to the lateral centerline IT of the fastening member 48 allows to provide the directionality of the shaped tab 51. The symmetricalness of the shaped upper edge 126 and the shaped lower edge 128 with respect to the longitudinal centerline L2 of the shaped tab 51 when relatively shifted In the longitudinal centerline L2 allows to continuously manufacture a fastening member easily and inexpensively without forming a trim.

The directionality of the shaped tab 51 can be generally recognized by the shape of the distal portion 120 of the shaped tab 51. The distal portion 120 of the shaped tab 51 shown in FIG. 6 is designed to provide downwardness of directionality as indicated by the arrow M. More concretely, the directionality can be recognized by specific shapes of the distal upper edge extending between the point A and the point C in the distal portion 120 and of the distal lower edge extending between the point C and the point B in the distal portion 120. It is convenient to compare the shape of the distal upper edge and the distal lower edge by the greatest distance from the center point X of the shaped tab 51. As shown in FIG. 6, the distal upper edge has a point G thereon which is spaced at the greatest distance from the center point X. The distal lower edge has a point H thereon which is spaced at the greatest distance from the center point X. The greatest distance between the point H and the center point X is preferably greater than the greatest distance between the point G and the center point X. Because of such difference of the distance from the center point X, the user recognizes directionality of the distal portion 120. It is preferable that tire greatest distance between the center point X and the point H is present at an angle S of between about 30 degree and about 60 degree downwardly with respect to the lateral centerline T2. It is also preferable that the greatest distance between the center point X and the point G is present at an angle T of between about 30 degree and about 60 degree upwardly with respect to the lateral centerline T2. It is even more preferable that the greatest distance between the center point X to the point H is not less than about 120% of the greatest distance between the center point X and Pre point G. It is also preferable that the greatest distance between the center point X to the point H is not more than about 200% of the greatest distance between the center point X and the point G.

The distal portion 120 of the shaped tab 51 may preferably have an upper rounded corner 130 and a lower rounded comet 132 which are adjacent the point G and point H, respectively. It is preferable that the upper rounded come 130 has a greater radius of curvature than the lower rounded corner 132. This also contributes to define the shape of shaped tab 51 to provide directionality.

The proximal portion 122 of the shaped tab 51 may have a recess 134 on the shaped upper edge 126 and a recess 136 on the shaped lower edge 128. The recess 134 extends between the point D and the point A on the shaped upper edge 126 and has a symmetric shape with the lower rounded corner 132 extending between the point E and B when relatively shifted in the longitudinal direction. At least a part of the recess 136 extends between the point B and die point F on the shaped lower edge 128 and has a symmetric shape with the upper rounded corner 130 extending between the point A and the point E. The recess 134 and/or the recess 136 effectively reduces the wrinkles, which are created in the ear panel 49 by the laterally pulling force, to be transmitted into the upper edge and/or the lower edge of the shaped tab 51, and helps the laterally pulling force to concentrate into the center portion of the shaped tab 51 along tire lateral centerline T2. Thus, as the wrinkles are not transmitted into the upper edge and/or the lower edge of the shaped tab 51, especially of the distal portion 120, the risk of removal of the shaped tab 51 caused by the wrinkles can be reduced.

Figure 8:
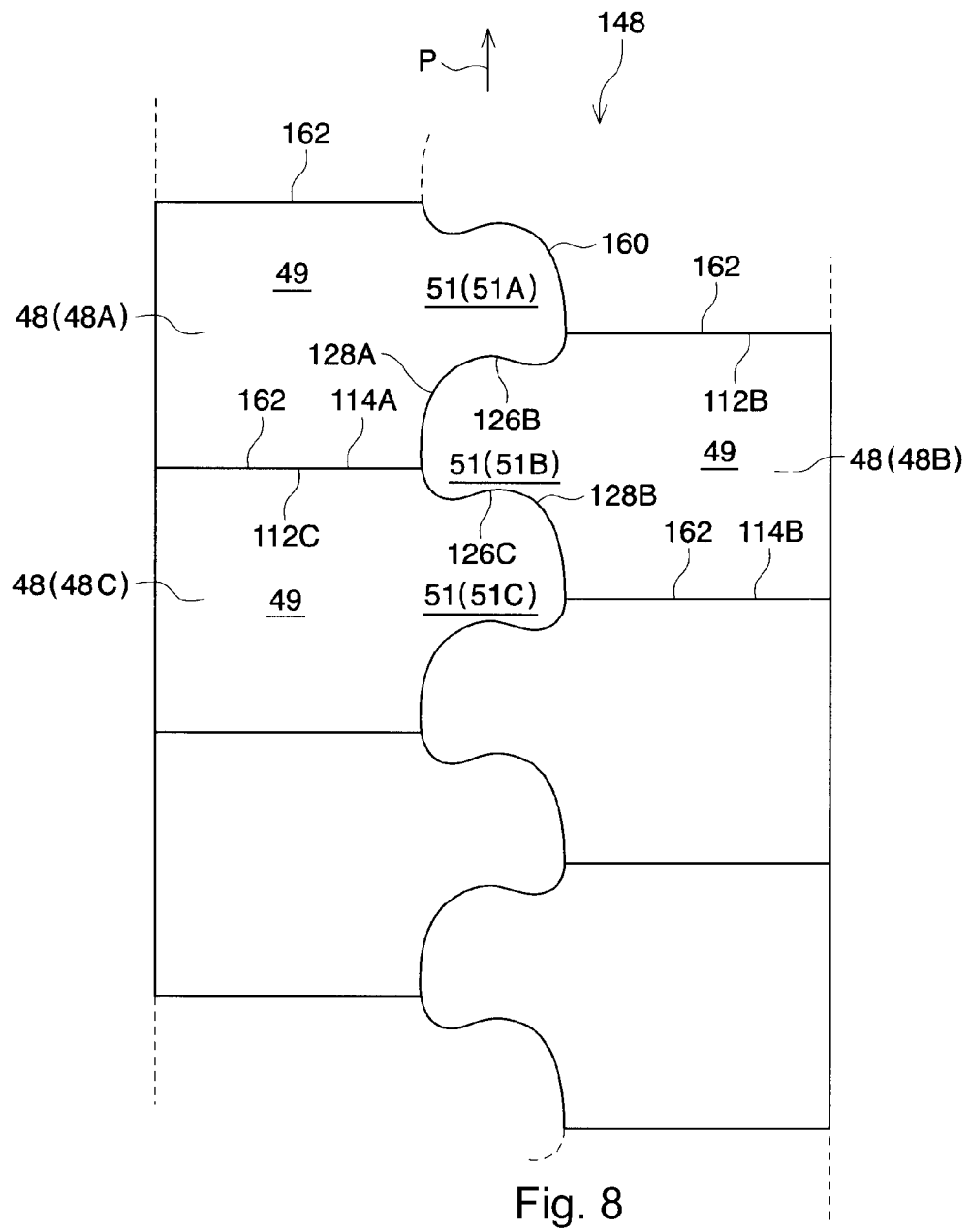
FIG. 8 is a schematic view of a process forming a plurality of fastening members.

FIG. 8 shows a schematic view of a process forming a plurality of fastening members. In FIG. 8, the fastening member web 148 is provided in the direction indicated by the arrow P. The fastening member web 148 has preferably been provided with a fastening material such as a book fastening material and/or adhesive material. The fastening member web 148 is cut along a shaped cut line 160 generally extending in the longitudinal direction and cut along a lateral cut line 162 to obtain a plurality of fastening members 48. A pair of fastening members 48 can be joined to the opposite longitudinal side edges 56 of the chassis 54 as shown in FIG. 3. The lateral cut line 162 forms the lateral lower edge 114A of the preceding fastening member 48A and the lateral upper edge 112C of tire following fastening member 48C en the left side. The shaped cut line 160 forms the contour edge 124 of the shaped tab 51. In the embodiment shown in FIG. 8, the shaped tab SIB of the fastening member 48B on the right side has the shaped upper edge 126 B and the shaped lower edge 128B, The shaped upper edge 126B corresponds to the shaped lower edge 128A of the shaped tab 51A of the preceding fastening member 48A on the left side. The shaped lower edge 128B corresponds to the shaped upper edge 126C of the shaped tab SIC of the following fastening member 48C on the left side. Thus, the specific configuration of the fastening member allows to continuously manufacture a fastening member easily and inexpensively without forming any trim as well as providing directionality of the fastening member.

Figure 9:
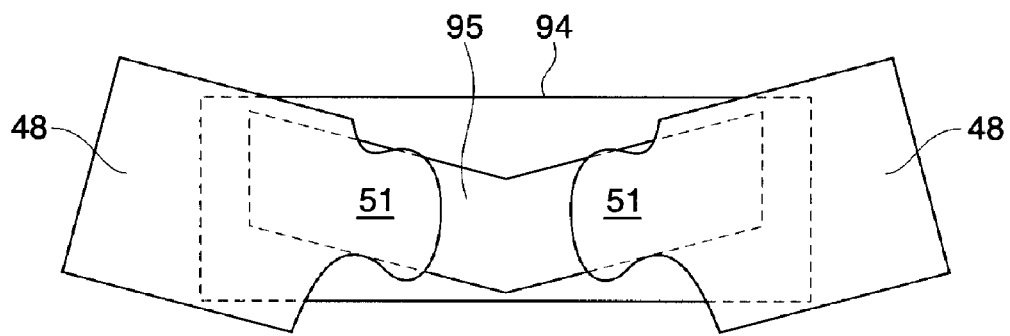
FIG. 9 is a schematic front view showing the fastening member joined to the landing zone member.

The fastening member 48 having directionality is especially useful when the fastening member 48 is joined to the landing zone member 94 to form a closure of the diaper 20. As shown in FIG. 9, the landing zone member 94 is provided in the front waist region (not shown in FIG. 9), Because the shaped tab S1 of the fastening member 48 is provided with downwardness of directionality M as explained above, the user tends to pull the shaped tab 51 downwardly whereby the "angled" line of tension about the wearer is easily formed. The landing zone member 94 in FIG. 9 may be provided with an angled guide means 95 to Indicate the direction of the fastening member 48 to more easily form the "angled" line of tension about the wearer.

Figure 10:
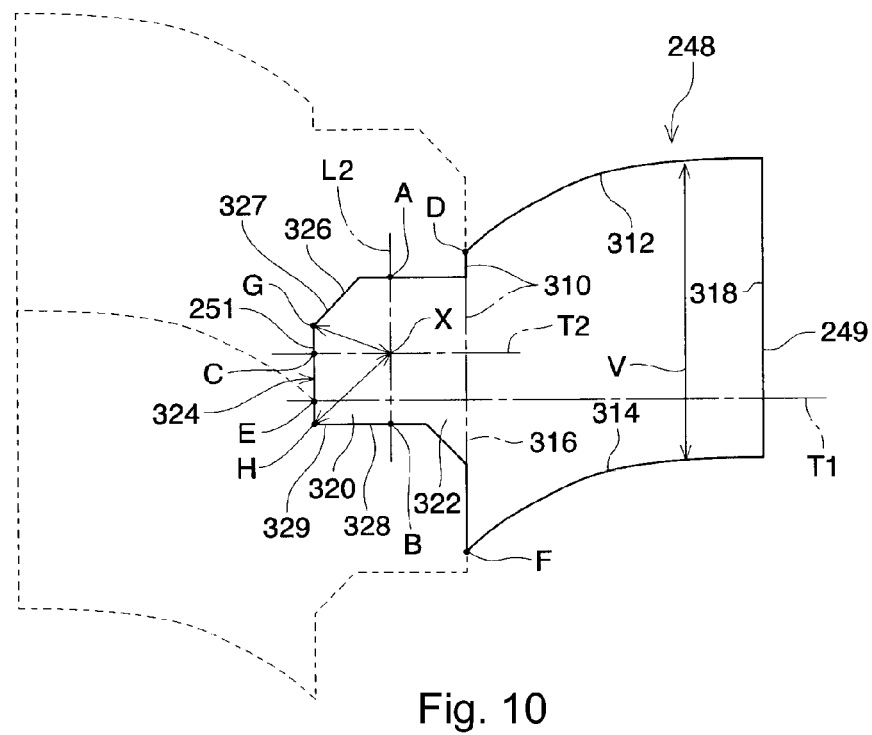
FIG. 10 is an alternative embodiment of a fastening member.

Many alternatives are possible in forming a fastening member of the present invention while only representative examples are described herein below. FIG. 10 shows an alternative embodiment of a fastening member. The fastening member 248 comprises the base panel or ear panel 249 and the shaped tab 251 sectioned by the partition line 310 extending in the longitudinal direction. The ear panel 249 has a lateral upper edge 312, a lateral lower edge 314, a longitudinal leading edge 316 and a longitudinal trailing edge 318. While the lateral upper edge 312 and the lateral lower edge 314 are curved as shown in FIG. 10, the longitudinal length V therebetween remains constant along the lateral direction of the ear panel 249. The contour edge 324 of the shaped tab 251 is formed by a combination of straight lines as shown in FIG. 10. The shaped tab 251 also has a distal portion 320 and a proximal portion 322.

The contour edge 324 of the shaped tab 251 comprises a shaped upper edge 326 and a shaped lower edge 328. The shaped upper edge 326 extends from a point D where the contour edge 324 and the partition line 310 intersect in the upper half of the fastening member 248 to a point E where the contour edge 324 and the lateral centerline T1 of the fastening member 248 intersect. The shaped lower edge 328 extends from the point E to a point F where the contour edge 324 and the partition line 310 intersect in the lower half of the fastening member 248. The shaped upper edge 326 and the shaped lower edge 328 are asymmetric with respect to the lateral centerline T1 of the fastening member 248 as shown in FIG. 10. The shaped upper edge 326 and the shaped rower edge 328 are symmetric with respect to the longitudinal centerline L2 of the shaped tab 251 when relatively shifted in the longitudinal direction. It is preferable in FIG. 10 that the greatest distance between the point H and the center point X is greater than the greatest distance between the point G and the center point X. The shaped upper edge 326 of the shaped tab 251 has a tapered, inclined distal upper corner 327 while the shaped lower edge 328 maintains the shape of the distal lower corner 329 having a right angle. This contrast of the shape of the distal upper corner 327 and the distal lower center 329 also contributes to provide directionality of the shaped tab 251. Further, in the embodiment shown in FIG. 10, the proximal portion 322 of the shaped tab 251 has no recess on the shaped upper edge 326 and no recess on the shaped lower edge 328.

Figure 11:
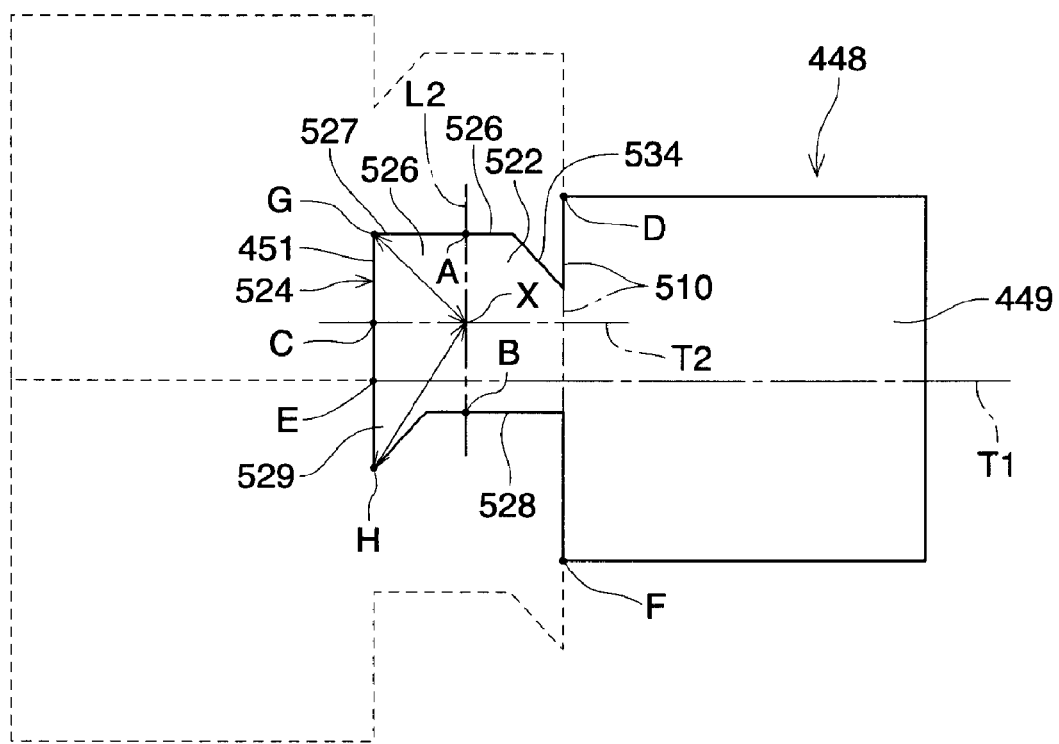
FIG. 11 is an another alternative embodiment of a fastening member.

FIG. 11 also shows an alternative embodiment of a fastening member. This embodiment of the fastening member 448 also comprises the base panel or ear panel 449 and the shaped tab 451 sectioned by the partition line 510 extending in the longitudinal direction. The contour edge 524 of the shaped tab 451 is formed by a combination of straight lines as shown in FIG. 11. The shaped tab 451 also has a distal portion 520 and a proximal portion 522.

The contour edge 524 of the shaped tab 451 comprises a shaped upper edge 526 and a shaped lower edge 528. The shaped upper edge 526 extends from a point D where the contour edge 524 and the partition line 510 intersect in the upper half of the fastening member 448 to a point E where the contour edge 524 and the lateral centerline 10 of the fastening member 448 intersect. The shaped lower edge 528 extends from the point E to a point F where the contour edge 524 and the partition line 510 intersect in the lower half of the fastening member 448, The shaped upper edge 526 and the shaped lower edge 528 are asymmetric with respect to the lateral centerline T1 of the fastening member 448 as shown in FIG. 11. The shaped upper edge 526 and the shaped lower edge 528 am symmetric with respect to the longitudinal centerline 12 of the shaped tab 451 when relatively shifted In the longitudinal direction, it is preferable in FIG. 11 that the greatest distance between the point B and the center point X is greater than the greatest distance between the point G and the center point X. The shaped lower edge 528 of the shaped tab 451 has a protrusion 529 protruding generally downwardly while the shaped upper edge 526 has the shape of the distal upper corner 527 having a right angle. This contrast of the shape of the distal upper corner 527 and the protrusion 529 also contributes to provide directionality of the shaped tab 451. Further, in the embodiment shown in FIG. 11, the proximal portion of the shaped tab 451 has a recess 534 on the shaped upper edge 526 and no recess on the shaped lower edge 528.

Figure 12:
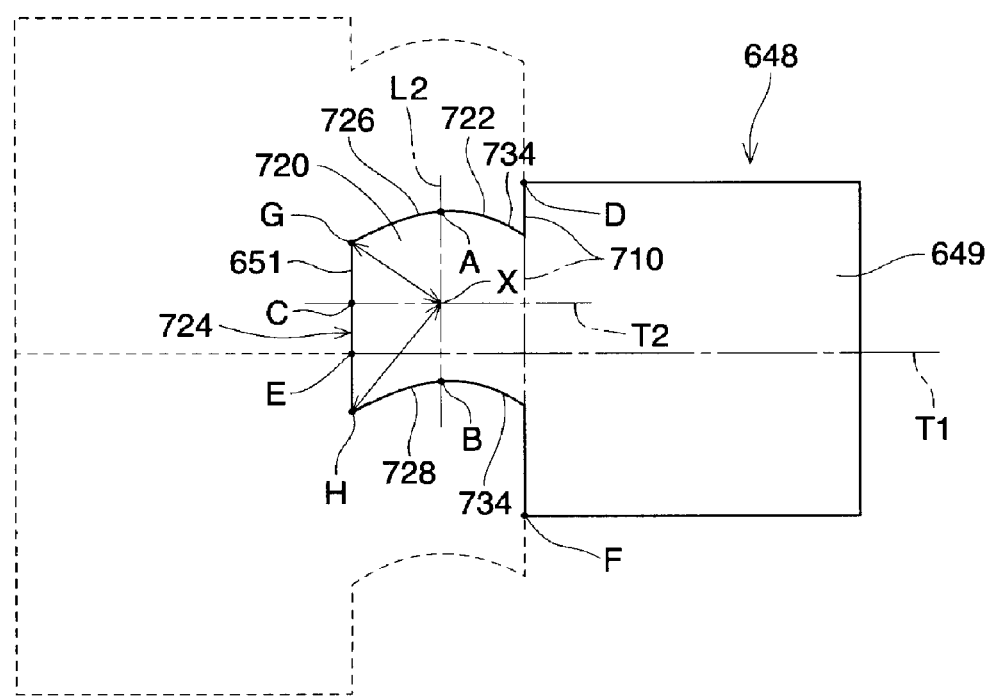
FIG. 12 is a further alternative embodiment of a fastening member.

FIG. 12 further shows an alternative embodiment of a fastening member. This embodiment of the fastening member 648 also comprises die base panel or ear panel 649 and the shaped tab 651 sectioned by the partition line 710 extending in the longitudinal direction. The shaped tab 651 also has a distal portion 720 and a proximal, portion 722.

The contour edge 724 of the shaped tab 651 comprises a shaped upper edge 726 and a shaped lower edge 728. The shaped upper edge 726 extends from a point D where the contour edge 724 and the partition line 710 intersect in the upper half of the fastening member 648 to a point E where the contour edge 724 and the lateral centerline T1 of the fastening member 648 intersect. Use shaped lower edge 728 extends from the point E to a point F where the contour edge 724 and the partition line 710 intersect. In the lower half of the fastening member 648. The shaped upper edge 726 and the shaped lower edge 728 are asymmetric with respect to the lateral centerline T1 of the fastening member 648 as shown in FIG. 12. The shaped upper edge 726 and the shaped lower edge 728 are symmetric with respect to the longitudinal centerline L2 of the shaped tab 651 when relatively shifted in the longitudinal direction. It is preferable in FIG. 12 that the greatest distance between the point H and the center point X is greater than the greatest distance between the point G and the center point X. The shaped upper edge 726 in the distal portion 720 (i.e., between the point A and the point G) and the shaped lower edge 728 in the distal portion 720 (i.e., between the point H and the point B) are both inclined downwardly as it is apart laterally away from the proximal portion 722. This shape of the shaped upper edge 726 and the shaped lower edge 728 in the distal portion 720 also contributes to provide directionality of the shaped tab 651. Further, in the embodiment shown in FIG. 12, the proximal portion of the shaped tab 651 has a recess 734 on the shaped upper edge 726 and a recess 734 on the shaped lower edge 728.

Figure 13:
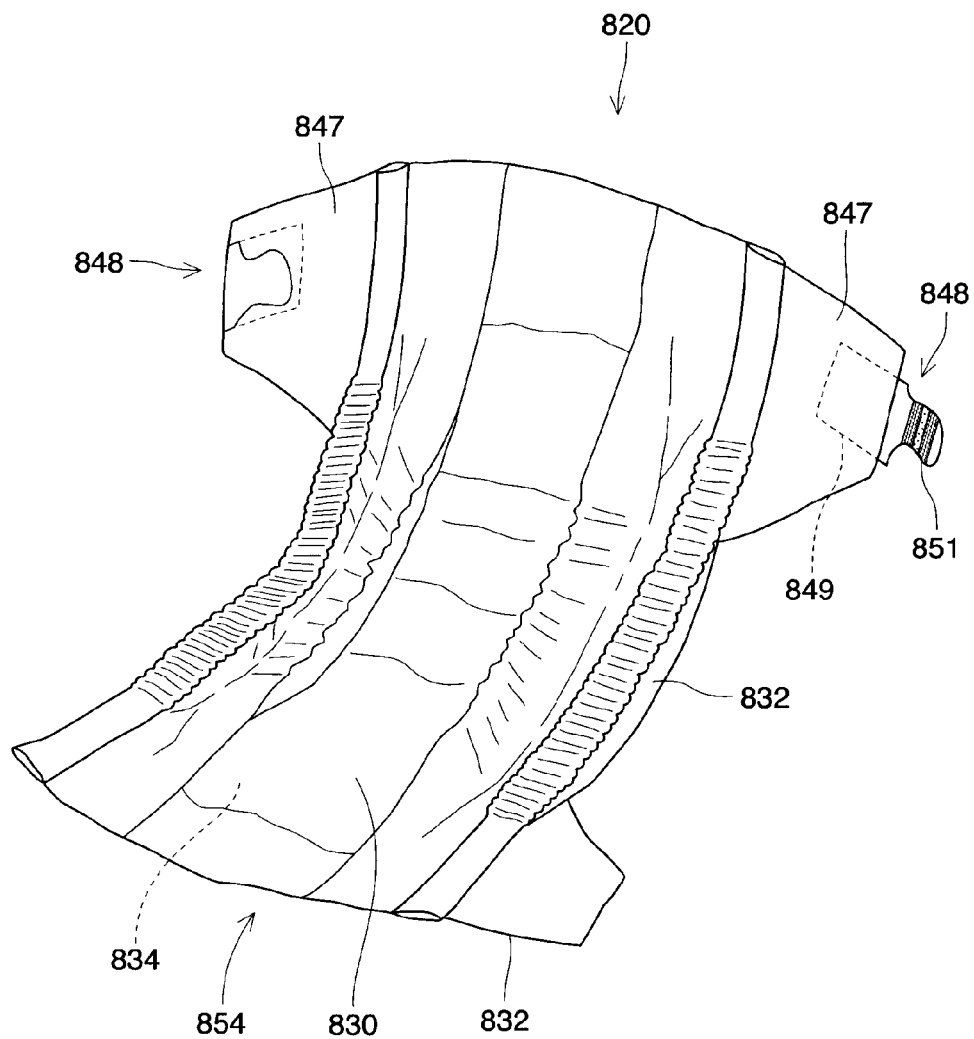
FIG. 13 is a perspective view of an alternative embodiment of a diaper having an alternative fastening member.

FIG. 13 shows an alternative embodiment of a diaper having a fastening member. The diaper 820 comprises a chassis 854 and a side panel 847 joined to the chassis 854. The chassis 854 has a liquid permeable topsheet 830, a liquid impermeable backsheet 832, and an absorbent core 834. In the embodiment shown in FIG. 13, the side panel 847 is formed with an integral extension of the backsheet 832 (e.g., an extension of a liquid impermeable film, or an extension of an outer nonwoven covering die liquid impermeable film). Therefore, the backsheet 832 of the diaper 820 has a generally hourglass shape having a narrow crotch region. The diaper 820 is also provided with the fastening member 848. The fastening member 848 is provided in the form of a fastening tape and comprises a shaped tab 851 and a base panel 849. The most portion of the base panel 849 is used to join the fastening member 848 to the side panel 847.

While particular embodiments of the present invention have been illustrated and described, it would be apparent to those skilled in the art that various other changes and modifications can be made without departing from the spirit and scope of the present invention. It is therefore intended to cover in the appended claims all such changes and modifications that are within the scope of this invention.

What is claimed is:

1. A fastening member extending in a longitudinal direction and in a lateral direction and having a lateral centerline, the fastening member comprising an ear panel and a tab extending laterally from the ear panel, wherein the tab has a longitudinal centerline, a lateral centerline, a distal portion and a proximal portion, the tab comprises leading, connective and trailing portions and a fastening material disposed on said connective portion of said tab, wherein said connective portion is stiffer than said ear panel, wherein said fastening material comprises a hook fastening material comprising a base joined to the connective portion and a plurality of hooks extending from said base, said hook fastening material having an inboard side edge, an outboard side edge, an upper edge, and a lower edge, wherein at least one of said upper, and lower edge of said hook fastening material is not parallel to said lateral centerline of said tab.

2. The fastening member according to claim 1 wherein said connective portion comprises a material chosen from at least one of a plastic film, a woven, and a nonwoven material.

3. The fastening member according to claim 2 wherein said ear panel comprises a nonwoven material and a film.

4. The fastening member according to claim 3 wherein said fastening member is folded inwardly such that some of said plurality of hooks of said hook fastening material engage the nonwoven material of said ear panel.

5. The fastening member according to claim 4 wherein said film of said ear panel comprises an elastomeric material.

6. The fastening member according to claim 2 wherein said ear panel comprises a zero strain stretch laminate.

7. The fastening member according to claim 6 wherein said zero strain stretch laminate comprises a nonwoven material and a film.

8. The fastening member according to claim 7 wherein said fastening member is folded inwardly such that said fastening material engages the nonwoven material of said ear panel.

9. The fastening member according to claim 8 wherein said film of said ear panel comprises an elastomeric material.

10. The fastening member according to claim 4 wherein said ear panel and said tab are formed with separate materials joined to one another.

11. The fastening member according to claim 4 wherein at least a portion of said shaped tab is integrally formed with said ear panel.

12. The fastening member according to claim 2 wherein said fastening material further comprises an adhesive.

13. The fastening member according to claim 2 wherein said fastening member is folded along a line that is parallel to the longitudinal centerline of the tab.

14. The fastening member according to claim 13 wherein said fastening member is folded along a line positioned on said tab.

15. The fastening member according to claim 14 wherein said fastening member is folded along a line positioned on said connective portion of said tab.

16. The fastening member according to claim 11 wherein said connective portion comprises a material that is different from a material of said ear panel.

17. An absorbent article comprising a fastening member according to claim 1.

18. The absorbent article according to claim 17 wherein said absorbent article comprises a topsheet, a backsheet and an absorbent core positioned between said topsheet and said backsheet and wherein said ear panel is joined to said backsheet.

19. The absorbent article according to claim 17 wherein said absorbent article comprises a front and back waist regions wherein said front waist region comprises a landing zone member and wherein said ear panel is joined to said back waist region.

20. The fastening member according to claim 1 wherein at least one of said upper, and lower edges of said hook fastening material is concave relative to the intersection point of said longitudinal and lateral centerlines of said shaped tab.

* * * * *